United States Patent [19]

Ward

[11] 4,140,793
[45] Feb. 20, 1979

[54] GUANIDINE DERIVATIVES

[75] Inventor: Terence J. Ward, Slough, England

[73] Assignee: John Wyeth & Brother, Ltd., Taplow, England

[21] Appl. No.: 801,973

[22] Filed: May 31, 1977

[30] Foreign Application Priority Data
Jun. 5, 1976 [GB] United Kingdom ............... 23331/76
Jan. 26, 1977 [GB] United Kingdom ................. 3056/77

[51] Int. Cl.² .................. C07D 207/06; H61K 31/40; C07D 207/08; C07D 207/10
[52] U.S. Cl. .............................. 424/274; 260/326.43; 424/251; 424/273 R; 544/331; 544/332; 548/316
[58] Field of Search ................... 260/326.43, 326.5 L; 424/274

[56] References Cited
U.S. PATENT DOCUMENTS
3,189,601   6/1965   Mull ............................. 260/326.43

Primary Examiner—Nicholas S. Rizzo
Assistant Examiner—Mary Lee
Attorney, Agent, or Firm—Arthur E. Wilfond

[57] ABSTRACT

The invention concerns novel guanidine derivatives of the general formula (I)

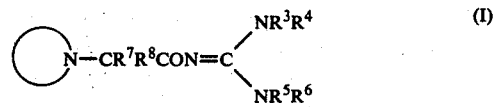

or pharmaceutically acceptable acid addition salts thereof, where 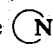 represents

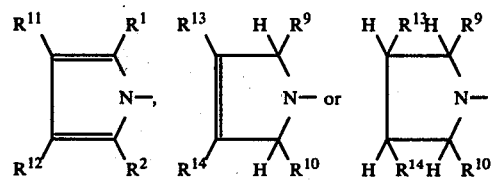

wherein $R^1$ and $R^2$ each represent hydrogen, lower alkyl, trifluoromethyl or halogen and $R^{11}$ and $R^{12}$ each represent hydrogen, lower alkyl, trifluoromethyl or halogen with the proviso that when one or both $R^{11}$ or $R^{12}$ groups represent halogen then $R^1$ and $R^2$ each represent lower alkyl, trifluoromethyl or halogen, $R^9$ and $R^{10}$ each represent hydrogen, lower alkyl or trifluoromethyl and $R^{13}$ and $R^{14}$ each represent hydrogen, lower alkyl, trifuoromethyl or halogen with the proviso that when one or both $R^{13}$ and $R^{14}$ groups represent halogen then $R^9$ and $R^{10}$ each represent lower alkyl or trifluoromethyl and $R^7$ and $R^8$ each represent hydrogen or lower alkyl and $R^3$, $R^4$, $R^5$ and $R^6$ each represent hydrogen or lower alkyl or $R^4$ and $R^6$ are each hydrogen and $R^3$ and $R^5$ together represent dimethylene or trimethylene. The guanidine derivatives lower blood pressure in warm-blooded animals.

11 Claims, No Drawings

GUANIDINE DERIVATIVES

This invention relates to novel guanidine derivatives, to processes for their preparation and to pharmaceutical compositions containing them.

The novel compounds of the present invention are guanidine derivatives of the general formula (I)

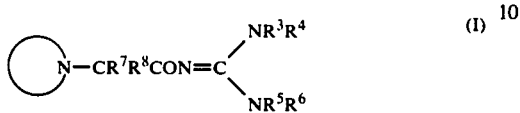

or pharmaceutically acceptable acid addition salts thereof, where

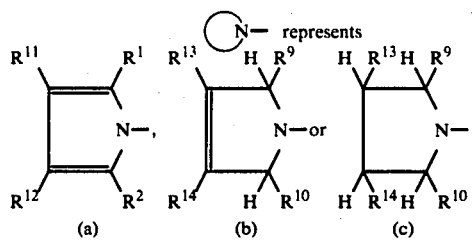

wherein $R^1$ and $R^2$ which may be the same or different each represent hydrogen, lower alkyl, the trifluoromethyl or halogen and $R^{11}$ and $R^{12}$ which may be the same or different each represent hydrogen, lower alkyl trifluoromethyl or halogen with the proviso that when one or both $R^{11}$ or $R^{12}$ groups represent halogen then $R^1$ and $R^2$ each represent lower alkyl, trifluoromethyl or halogen, $R^9$ and $R^{10}$ which may be the same or different each represents hydrogen, lower alkyl or trifluoromethyl and $R^{13}$ and $R^{14}$ which may be the same or different each represents hydrogen, lower alkyl, trifluoromethyl or halogen with the proviso that when one or both $R^{13}$ and $R^{14}$ groups represent halogen then $R^9$ and $R^{10}$ each represent lower alkyl or trifluoromethyl and $R^7$ and $R^8$ are the same or different and each represent hydrogen or lower alkyl and $R^3$, $R^4$, $R^5$ and $R^6$ are the same or different and each represent hydrogen or lower alkyl or $R^4$ and $R^6$ are each hydrogen and $R^3$ and $R^5$ together represent dimethylene or trimethylene such that

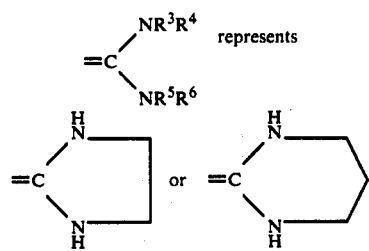

The term "lower" as used herein means that the radical referred to contains 1 to 6 carbon atoms. Preferably the radical contains 1 to 4 carbon atoms.

The compounds of the invention in which

has the meaning (a) are pyrrole derivatives. Thus in one aspect the present invention provides pyrrole derivatives of general formula (II)

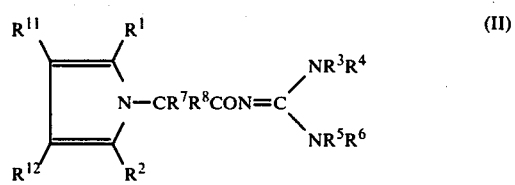

and pharmaceutically acceptable acid addition salts, thereof, wherein $R^1$, $R^2$, $R^3$, $R^4$, $R^5$, $R^6$, $R^7$, $R^8$, $R^{11}$ and $R^{12}$ the meanings given above. In connection with formula (II), $R^1$ and $R^2$ can be hydrogen, lower alkyl (eg. methyl ethyl, propyl or butyl), trifluoromethyl or halogen (e.g. chlorine or bromine). Preferably $R^1$ and $R^2$ are both the same; for example they may be both methyl. $R^{11}$ and $R^{12}$ can be hydrogen, lower alkyl (e.g. methyl, ethyl, propyl or butyl) or trifluoromethyl. $R^{11}$ and $R^{12}$ can also be halogen (eg. chlorine or bromine) when neither $R^1$ and $R^2$ is hydrogen. Preferably both $R^{11}$ and $R^{12}$ are hydrogen.

The compounds of the invention in which

has meaning (b) and (c) are respectively 2,5-dihydro-1H-pyrrol-1-yl and pyrrolidinyl-1-yl derivatives. Thus in a further aspect the invention provides 2,5-dihydro-1H-pyrrol-1-yl derivatives of general formula (III) below and pyrrolidinyl-1-yl derivatives of general formula (IV) below and their pharmaceutically acceptable acid addition salts:

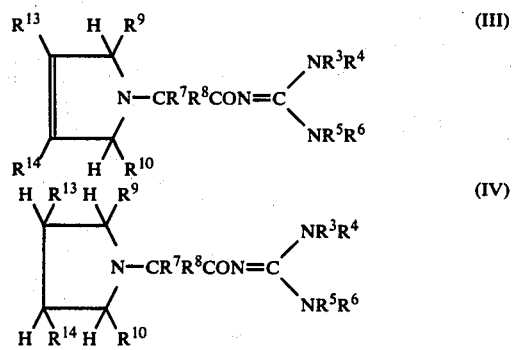

In formulae (III) and (IV) $R^3$, $R^4$, $R^5$, $R^6$, $R^7$, $R^8$, $R^9$, $R^{10}$ and $R^{13}$ and $R^{14}$ have the meanings given above. Thus $R^9$ and $R^{10}$ are hydrogen, trifluoromethyl or lower alkyl (eg methyl), ethyl, propyl or butyl). Preferably $R^9$ and $R^{10}$ are both the same; for example they may be both methyl. $R^{13}$ and $R^{14}$ can be hydrogen, lower alkyl (eg. methyl, ethyl, propyl or butyl) or trifluoromethyl. $R^{13}$ and $R^{14}$ can also be halogen (eg. chlorine or bromine) when neither $R^9$ nor $R^{10}$ is hydrogen. Preferably both $R^{13}$ and $R^{14}$ are hydrogen.

In general formula (I), (II), (III) and (IV) when any of $R^3$, $R^4$, $R^5$, $R^6$, $R^7$, and $R^8$ are lower alkyl they can be, for example, methyl, ethyl, propyl or butyl. Preferably each group $R^3$, $R^4$, $R^5$, $R^6$, $R^7$ and $R^8$ is hydrogen.

Although the compounds of the invention have been shown in general formulae (I), (II) and (IV) as existing in the acylimino form it is possible that the compounds exist in other tautomeric forms or mixtures of such forms. For example, possible structures of the compounds in which $R^3$, $R^4$, $R^5$, $R^6$, $R^7$ and $R^8$ are all hydrogen include the acylamino structure (Ia)

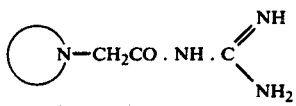
(Ia)

and the enol forms (Ib), (Ic) or (Id)

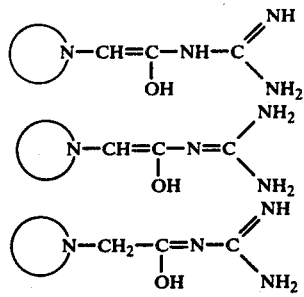

Where in this specification there is used a name or formula implying any particular tautomeric form it is to be understood that the name or formula includes any of the other alternatives forms or a mixture of such forms.

The compounds of the invention may contain one or more asymmetric carbon atoms and hence can exist in more than one isomeric form. Such forms can be obtained or separated by standard procedures. For example, the compounds of general formula (III) and (IV) in which $R^9$ and $R^{10}$ are both trifluoromethyl or identical lower alkyl groups can exist in cis or trans forms. Either the cis or the trans form can be obtained by suitable choice of starting material in the processes hereinafter described. The trans form will normally be obtained as a racemate of the d- and l- enantiomorphs which can be separated by standard methods of resolution if desired. The compounds of general formula (III) and (IV) in which $R^{13}$ and $R^{14}$ are both hydrogen and $R^9$ and $R^{10}$ are different lower alkyl groups or one is trifluoromethyl and the other lower alkyl contain two asymmetric carbon atoms and hence can exist in four optically active forms. Normally the compounds are prepared in the form of racemates which can, if desired, be resolved by standard methods. Compounds of general formula (III) and (IV) in which $R^{13}$ and $R^{14}$ are both hydrogen and in which one of $R^9$ and $R^{10}$ is lower alkyl and the other is hydrogen contain one asymmetric carbon atom and hence such compounds may be in the form of the optically active enantiomers or as mixtures of enantiomers, e.g. racemates. If desired, the racemates may be resolved by standard methods described in the literature. A further asymmetric carbon atom occurs in compounds of formula (IV) in which $R^{13}$ or $R^{14}$ is other than hydrogen.

The compounds of the invention can be prepared by a process in which a reactive derivative of an acid of general formula (V)

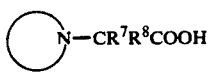
(V)

(where

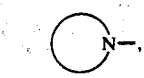

$R^7$ and $R^8$ have the meanings given above) or an acid addition salt thereof is reacted with a guanidine of the formula

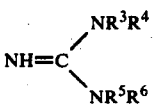
(VI)

(where $R^3$, $R^4$, $R^5$ and $R^6$ are each hydrogen or lower alkyl) or with 2-amino-imidazoline or 2-amino-1,4,5,6-tetrahydropyrimidine.

A possible reactive derivative of the acid of general formula (V) is the acid chloride but a preferred reactive derivative is an ester, in particular an ester of general formula (Va),

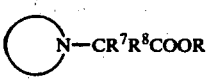
(Va)

(wherein

$R^7$ and $R^8$ are as defined above and R is a lower alkyl, e.g. methyl or ethyl), or an acid addition salt thereof.

The reactive derivatives of the acid of general formula (V) may be prepared in a manner known for preparing analogous compounds. For example the pyrrole derivatives of general formula (V) [

has meaning (a)] can be prepared by the method disclosed in German Offenlengunsscrift No. 2,312,006. The pyrrole derivatives can also be prepared by an alternative method in which a dicarbonyl compound of general formula

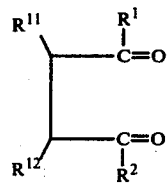

(where $R^1$ and $R^2$ are each hydrogen, trifluoromethyl or lower alkyl and $R^{11}$ and $R^{12}$ are each hydrogen, trifluoromethyl or lower alkyl) or a functional derivative thereof is reacted with a lower alkyl ester of an amino acid of formula $NH_2CR^7R^8COOH$, e.g. a lower alkyl ester of glycine or alanine. When $R^1$ and $R^2$ are both hydrogen the functional derivative of the compound of general formula (IV) may be a 2,5-dialkoxytetrahydrofuran of general formula

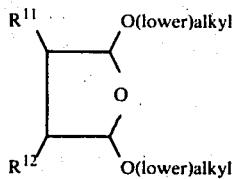

In order to prepare a pyrrole derivative of general formula (Va) in which at least one of the $R^1$, $R^2$, $R^{11}$ and $R^{13}$ groups is halogen the corresponding compound in which the group is hydrogen may be halogenated. For example the compound can be halogenated with sulphuryl chloride. By suitable choice of, and proportions of, reactants it is possible to halogenate in the 2 and/or 5-position and also in the 3 and/or 4-position. If the starting material contains trifluoromethyl or lower alkyl substituents in the 2 and 5-position then halogenation will occur in the 3 and/or 4-positions.

The 2,5-dihydro-1H-pyrrol-1-yl derivatives [

has meaning (b)] of general formula (Va) can be prepared, for example, by alkylating a dihydropyrrole of general formula

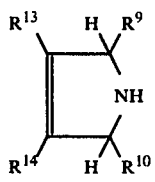 (IX)

(where $R^9$, $R^{10}$, $R^{13}$ and $R^{14}$ have the meanings given above with a haloacid of general formula

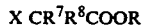

X CR⁷R⁸COOR (where R, $R^7$ and $R^8$ are as defined above and X is halo, preferably bromo or chloro). The starting materials of general formula (IX) are known compounds or may be prepared in a manner known for preparing analogous compounds, for example, by reduction (eg. with zinc and hydrochloric acid of a corresponding pyrrole of general formula (X)

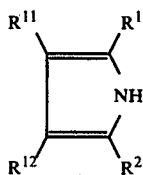 (X)

(where $R^1$, $R^2$, $R^{11}$ and $R^{12}$ are as defined above).

The pyrrolidinyl-1-yl derivatives [

has meaning (c)] of general formula (Va) may be prepared, for example, from the corresponding 2,5-dihydro-1H-pyrrol-1-yl derivatives, e.g. by catalytic hydrogenation. Alternatively a 2,5-dihydro-1H-pyrrol-1-yl derivative of general formula (Va) in which $R^{13}$ and $R^{14}$ are both hydrogen may be treated with halogen or a hydrogen halide to give a pyrrolidinyl-1-yl derivative of formula (Va) in which $R^{13}$ and/or $R^{14}$ is halogen.

Once an ester of the acid of general formula (V) or its acid addition salt has been prepared this may be converted into other reactive derivatives of the acid by standard procedures. For example, the ester of formula (Va) may be hydrolysed to the acid which, in turn may be reacted with thionyl chloride to give the acid chloride.

The compounds of general formula (I) in which $R^3$, $R^4$, $R^5$ and $R^6$ are each hydrogen or lower alkyl and $R^7$ and $R^8$ are both hydrogen may be prepared by an alternative procedure which comprises hydrolysing a compound of general formula

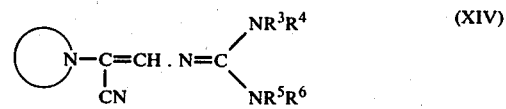 (XIV)

where

has the meaning defined in claim 1 and $R^3$, $R^4$, $R^5$ and $R^6$ are each hydrogen or lower alkyl and, if desired, converting a resulting base of general formula (I) into a pharmaceutically acceptable salt thereof.

The compounds of general formula (XIV) may be prepared by formylation (eg. by reaction with ethyl formate) of a nitrile of general formula (XI)

 (XI)

(where

is as defined above) followed by condensation of the resulting α-formyl compound with a guanidine of formula (VI). The nitriles of formula (XI) may be prepared by reaction of an alkali metal salt (eg. the potassium salt) of the pyrrole, dihydropyrrole or pyrrolidine of general formula

(where

is as defined above) with chloracetonitrile. An alternative method of preparing the nitriles of general formula (XI) comprises halogenating (eg with sulphuryl chloride) a nitrile of formula (XI) in which

represents

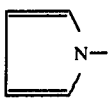

to give the corresponding 2,5-dihalo-nitrile compound. Alternatively the corresponding 2,5-di(lower)alkyl or di(trifluoromethyl) nitrile compound can be halogenated in the 3 and 4-positions. The nitrile compound of formula (XI) in which

represents

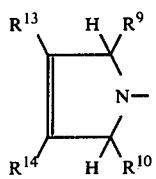

(where $R^9$ and $R^{10}$ are as defined above and $R^{13}$ and $R^{14}$ are halogen can be prepared by reduction (eg. with zinc and hydrochloric acid) of the corresponding pyrrole derivatives. The nitrile compound of formula (XI) in which

represents

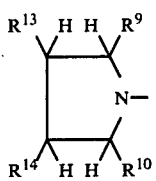

(in which $R^9$ and $R^{10}$ are as defined above and $R^{13}$ and $R^{14}$ are halogen) can be prepared by halogenation of the nitrile compound in which

represents

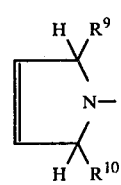

The compounds of the invention in which $R^3$ is hydrogen and $R^4$, $R^5$ and $R^6$ are each hydrogen or lower alkyl may be prepared by a further method which comprises reacting an isothiourea derivative of general formula (VII)

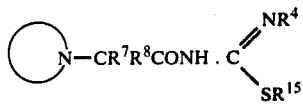  (VII)

(where

$R^7$ and $R^8$ are as defined in claim 1, $R^4$ is hydrogen or lower alkyl and $R^{15}$ is lower alkyl preferably methyl) with ammonia or an amine of formula $$NHR^5R^6 \qquad (XII)$$

(where $R^5$ and $R^6$ are each hydrogen or lower alkyl), and, if desired, converting a resulting base into a pharmaceutically acceptable salt thereof.

The isothioureas of general formula (VII) may be prepared by reacting an acyl chloride of general formula

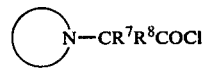  (XIII)

(where

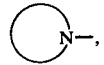

$R^7$ and $R^8$ are as defined above) with a S-(lower)alkylisothiourea, particularly S-methylisothiourea.

The compounds of the invention in which $R^3$ and $R^4$ are both hydrogen and $R^5$ and $R^6$ are each hydrogen or or lower alkyl can be prepared by a still further method which comprises reacting an acylcyanamide of general formula (VIII)

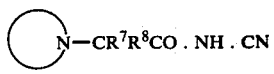  (VIII)

(where

$R^7$ and $R^8$ are as defined above) with ammonia or amine of general formula (XII) above and, if desired, converting a resulting base into a pharmaceutically acceptable acid addition salt thereof. The acylcyanamides of general formula (VIII) may be prepared by condensing an acyl chloride of formula (XIII) above with an alkaline metal or alkaline earth metal salt of cyanamide, eg. sodium or calcium cyanamide.

Compounds of the invention in which represents

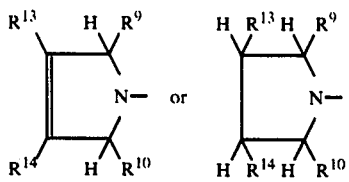

and in which $R^3$, $R^4$, $R^5$ and $R^6$ are hydrogen may be prepared by a still further method which comprises condensing a dihydropyrrole or pyrrolidine of general formula

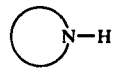

where

represents

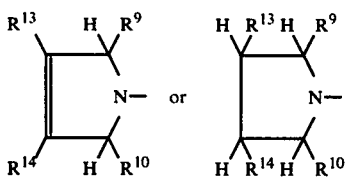

(where $R^9$, $R^{10}$, $R^{13}$ and $R^{14}$ are as defined above with a haloacetylguanidine of general formula

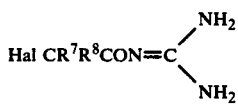

(where $R^7$ and $R^8$ are as defined above and Hal is chlorine or bromine) and, if desired, converting a resulting base of general formula (I) into a pharmaceutically acceptable acid addition salt thereof.

The compounds of the invention in which

represents

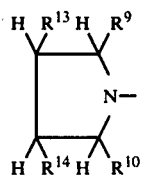

can be prepared by a still further process which comprises catalytically hydrogenating the compounds of the invention in which

represents

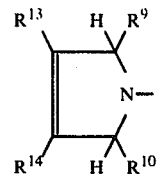

If in any of the processes described above the compound of the invention is obtained as an acid addition salt, the free base can be obtained by basifying a solution of the acid addition salt. Conversely if the compound of the invention is obtained as a free base in any of the above processes a pharmaceutically acceptable acid addition salt may be obtained by dissolving the free base in a suitable organic solvent and treating the solution with an acid, in accordance with conventional procedures for preparing acid addition salts from base compounds. Examples of acid addition salts include those formed from inorganic and organic acids such as sulphuric, hydrochloric, hydrobromic, phosphoric, tartaric, fumaric, maleic, citric, acetic, formic, methanesulphonic and p-toluenesulphonic acids. The compounds of the invention lower blood pressure as indicated by standard hypotensive or antihypertensive pharmacological procedures. For example, N-diaminomethylene-(2,5-dimethyl-1H-pyrrol-1-yl)acetamide, a representative compound of the invention, when administered to normotensive anaesthetised rats produced a fall of diastolic blood pressure of at least 30 mm Hg at 15 minutes after administration at dosages of less than 2 mg/kg in duplicate experiments. The compound also lowered the blood pressure of hypertensive rats when administered at 5 mg/kg per os. The compounds of the invention also possess hyperglycaemic activity as determined by a procedure in which the compounds are administered to normal male rats and blood samples are analysed for blood sugar prior to administration of the compound and at hourly intervals after administration. Hyperglycaemic agents can be of use for administration to patients who have too low a blood sugar concentration following, for example, administration of too large a dose of a hypoglycaemic agent such as insulin. Hyperglycaemic agents can also be used to produce hyperglycaemic animals which can be used in screening for hypoglycaemic compounds in pharmacological procedures.

Some of the compounds of the invention are also anti-ulcer agents which possess anti-secretory activity in the test of H. Shay, D. Sun and H. Greenstein, Gastroenterology, 1954, 26, 903-13. Compounds which possess anti-secretory activity are exemplified by N-diaminomethylene-(2,5-dimethyl-1H-pyrrol-1-yl)acetamide, N-diaminomethylene-(2,5-dichloro-1H-pyrrol-1-yl)acetamide and N-diaminomethylene-(trans-2,5-dihydro-2,5-dimethyl-1H-pyrrol-1-yl)acetamide. For example, N-diaminomethylene-(trans-2,5-dihydro-2,5-dimethyl-1H-pyrrol-1-yl)acetamide, shows potent antisecretory activity in the test of Shay et al at dosages as low as at least 5 mg/kg intraduodenally as indicated by the following results:

| Compound | Dose mg/kg (i-duod.) | % decrease | | |
|---|---|---|---|---|
| | | volume of gastric contents | conc. of acid | amount of free acid | total acid |
| N-diamino- | | | | | |

-continued

| Compound | Dose mg/kg (i-duod.) | % decrease volume of gastric contents | conc. of acid | amount of free acid | total acid |
|---|---|---|---|---|---|
| methylene-(trans-2,5-dihydro-2,5-dimethyl-1H-pyrrol-1-yl)acetamide | 5 | 72 | 39 | 79 | 72 |

The invention includes a pharmaceutical composition comprising a compound of general formula (I) or a pharmaceutically acceptable salt thereof in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by the carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilized by intramuscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredient; the unit dosage form can be a packaged compositions, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5mg. or less to 500 or more, according to the particular need and the activity of the active ingredient. The invention also includes the compounds in the absence of carrier where the compounds are in unit dosage form.

Pharmaceutical compositions containing compounds of the invention possessing antisecretory activity may be administered as anti-ulcer compositions. Those compositions may be administered orally in liquid or solid composition form and such compositions may include one or more antacid ingredients, e.g. aluminium hydroxide, magnesium hydroxide, bismuth carbonate, aluminium glycinate, calcium carbonate, magnesium trisilicate, sodium bicarbonate or the alumina gel described in U.K. Patent Specification No. 1,284,394.

The following Examples illustrate the invention and the preparation of intermediate compounds:

EXAMPLE 1

Methyl (2,5-dimethyl-1H-pyrrol-1-yl)acetate

A solution of hexan-2,5-dione (23 g.), glycine methyl ester hydrochloride (25 g.), and sodium acetate (16 g.) in acetic acid (100 cm$^3$) was heated under reflux for 1 hour. The mixture was then poured into water, extracted with ether, and the ethereal phase washed with sodium carbonate solution, dried, and evaporated to yield a brown oil. The product was then distilled under vacuum to give methyl (2,5-dimethyl-1H-pyrrol-1-yl)acetate as a colourless oil which crystallised on standing. (22.1 g.) b.p. 123°–129° C./15 mm, m.p. 44°–46° C.

EXAMPLE 2

N-Diaminomethylene-(2,5-dimethyl-1H-pyrrol-1-yl)acetamide

A solution of guanidine hydrochloride (5.7 g.) and sodium ethoxide (1.15 g. of sodium) in dry ethanol (60 cm$^3$) was stirred at room temperature for 1 hour. The precipitated sodium chloride was removed by filtration and washed with ethanol (10 ml.). Methyl (2,5-dimethyl-1H-pyrrol-1-yl) acetate (8.4 g.) was added to the combined filtrate and washing obtained above and the solution stoppered and stirred for 3.5 h., then cooled in ice and the precipitated solid collected by filtration. Crystallisation from ethanol, with filtration to remove insoluble impurities, gave N-diaminomethylene-(2,5-dimethyl-1H-pyrrol-1-yl) acetamide as straw coloured plates (6 g.) m.p. 198.5°–200° C. The hydrochloride (m.p. 228°–230° C.) was precipitated from warm ethanol on treatment with ethanolic hydrogen chloride.

EXAMPLE 3

N-Diaminomethylene-1H-pyrrole-1-yl acetamide

A solution of guanidine hydrochloride (2.85 g.) and sodium ethoxide (from 0.6 g. of sodium) in dry ethanol (30 cm$^3$) was stirred at room temperature for 1 hour. The precipitated sodium chloride was removed by filtration and washed with ethanol (5 cm$^3$). Methyl 1H-pyrrol-1-ylacetate (3.5 g.) was added to the combined filtrate and washings obtained above and the solution stoppered and stirred for 3.5 hours, then cooled in ice and the precipitated product collected by filtration.

Crystallization from methanol gave the title compound as white needles (1.8 g.) m.p. 213.5°–214° C. The hydrochloride m.p. 200°–201° C., was precipitated from a solution of the base in ethanol by addition of ethanolic hydrogen chloride.

EXAMPLE 4

Methyl (2,5-dichloro-1H-pyrrol-1-yl)acetate

A solution of sulphuryl chloride (10.8 g.) in dry ether (20 cm$^3$) was added dropwise to a stirred solution of methyl 1H-pyrrol-1ylacetate (5.6 g.) in dry ether (20 cm$^3$) maintained below 0° C. After addition was complete the reaction was stirred for a further 0.5 hour, without external cooling. Water and ether were then added, the ethereal phase was separated, washed with sodium carbonate solution, dried and evaporated. The residual oil was then distilled under vacuum to give methyl(2,5-dichloro-1H-pyrrol-1-yl)acetate as a light yellow oil (5.2 g.) b.p. 120°–121° C./15 mm.

EXAMPLE 5

N-Diaminomethylene-(2,5-dichloro-1H-pyrrol-1-yl)acetamide

A solution of guanidine hydrochloride (2.85 g) and sodium ethoxide (from 0.6 g. of sodium) in dry ethanol (30 cm$^3$) was stirred at room temperature for 1 hour. The precipitated sodium chloride was removed by filtration and washed with ethanol (5 cm$^3$). Methyl (2,5-dichloro-1H-pyrrol-2-yl)acetate (5.2 g) was added to the combined filtrate and washings obtained above and the solution stoppered and stirred for 3.5 hours, then cooled in ice and the precipitated title compound collected by filtration (2.3 g) m.p. 223°–225° C. The filtrate was evaporated and the residue crystallised from a mixture of ethanol (5 cm$^3$) and water (5 cm$^3$) to give further title product (1 g.) m.p. 223.5°–225° C. The hydrochloride of the title compound m.p. 204°–205° C., was precipitated from a solution of the base in ethanol by addition of ethanolic hydrogen chloride.

EXAMPLE 6

Methyl (trans-2,5-dihydro-2,5-dimethyl-1H-pyrrol-1-yl)acetate

Methyl bromoacetate (16.8 g, 0.11 mol) was added, dropwise, to a stirred mixture of 2,5-dimethyl-3-pyrroline (10 g, 0.1 mol), potassium carbonate (13.8 g, 0.1 mol), and dimethylformamide (25 cm$^3$) maintained below 30° C. by ice cooling. After addition was complete the mixture was cooled in ice for a further 1 h, then stirred at room temperature overnight. The reaction mixture was then diluted with water (50 cm$^3$) and the product extracted into ether. The ether extract was dried and evaporated to yield an oil* which was distilled under vacuum to give methyl (trans-2,5-dihydro-2,5-dimethyl-1H-pyrrol-1-yl)acetate (7 g) b.p. 89°–92° C./15 mm.

* G.l.c. shows this to contain a mixture of the cis and trans isomers in the ratio 1:3. The cis isomer could not be obtained pure from this distillation, but a sample was isolated by preparative g.l.c.

EXAMPLE 7

N-Diaminomethylene-(trans-2,5-dihydro-2,5-dimethyl-1H-pyrrol-1-yl)acetamide

A solution of guanidine hydrochloride (2.3 g, 0.024 mol) and sodium ethoxide (from 0.55 g, 0.024 mol of sodium) in absolute ethanol (24 cm$^3$) was stirred at room temperature for 1 h. The precipitated sodium chloride was removed by filtration and washed with ethanol (4 cm$^3$). Methyl (trans-2,5-dihydro-2,5-dimethyl-1H-pyrrol-1-yl)acetate (3.4 g, 0.02 mol from Example 6) was added to the combined filtrate and washings obtained above and the solution stoppered and stirred for 18 h. The reaction mixture was then evaporated and the residue crystallised from ethanol to give the product (1.25 g). The base was suspended in ethanol and acidified the ethanolic hydrogen chloride, the clear solution thus obtained was diluted with ethyl acetate and concentrated by evaporation to precipitate the title compound as the dihydrochloride (1.6 g.), m.p. 210°–211° C.(d).

EXAMPLE 8

2,5-Dichloro-N-(2-imidazolidinylidene)-1H-pyrrole-1-acetamide

Methyl (2,5-dichloro-1H-pyrrol-1-yl)acetate (2.08 g.) was added to a solution of 2-aminoimidazoline hydroiodide (3.2 g.) and sodium ethoxide (from 0.35 g. of sodium) in ethanol (10 cm$^3$). The solution was stirred at room temperature for 3 hr. and the precipitated title product collected by filtration (1.9 g.) m.p. 225°–227° C. The base was suspended in ethanol (25 cm$^3$) and acidified with ethanolic hydrogen chloride to give the hydrochloride of the title compound (1.9 g.) m.p. 225° C.(d).

EXAMPLE 9

Ethyl 2-(trans-2,5-dimethyl-2,5-dihydro-1H-pyrrol-1-yl)propionate

Ethyl 2-bromopropionate (9.8 g.) was added, dropwise, to a stirred mixture of trans-2,5-dimethyl-3-pyrroline (5 g.), potassium carbonate (6.9 g.), and dimethylformamide (12.5 cm$^3$) maintained below 30° C. by external cooling. After addition was complete the mixture was stirred at room temperature overnight. The mixture was then diluted with water (25 cm$^3$) and the product extracted into ether. The ether extract was dried and evaporated to give an oil which was distilled under vacuum to give ethyl 2-(trans-2,5-dimethyl-2,5-dihydro-1H-pyrrol-1-yl)propionate (2.5 g.) b.p. 90°–97° C./15 mm.

EXAMPLE 10

N-Diaminomethylene-2-(trans-2,5-dimethyl-2,5-dihydro-1H-pyrrol-1-yl)propionamide A solution of guanidine hydrochloride (2.0 g.) and sodium ethoxide (from 0.46 g. of sodium) in ethanol (12.5 cm$^3$) was stirred at room temperature for 1 h. The precipitated sodium chloride was removed by filtration and washed with ethanol (5 cm$^3$). Ethyl 2-(trans-2,5-dimethyl-2,5-dihydro-1H-pyrrol-1-yl) propionate (2.5 g.) was added to the combined filtrate and washings obtained above and the solution allowed to stand overnight. The reaction mixture was then evaporated and the residue partitioned between water (5 cm$^3$) and ether (10 cm$^3$). On cooling the crystalline title product separated, was collected by filtration, and washed with water and ether. The product was suspended in isopropyl alcohol and acidified with ethanolic hydrogen chloride to give the title compound as the dihydrochloride (0.5 g.) m.p. 206°–206.5° C.

EXAMPLE 11

Methyl (2,3,4,5-tetrachloro-1H-pyrrol-1-yl)acetate

A solution of sulphuryl chloride (5.4 g.) in dichloromethane (5 cm$^3$) was added, dropwise, to a stirred solution of methyl (1H-pyrrol-1-yl)acetate (1.39 g.) in dichloromethane (5 cm$^3$) maintained below 5° C. by an ice/salt bath. After addition was complete the cooling bath was removed and the solution stirred for a further 0.5 h. Aqueous sodium carbonate solution was then added and the organic phase separated, dried and evaporated to give a crystalline solid. The product was introduced onto a short column of alumina and eluted with cyclohexane to give methyl (2,3,4,5-tetrachloro-1H-pyrrolyl)acetate as white prisms (1.4 g.) m.p. 115° C.

EXAMPLE 12

N-Diaminomethylene-(2,3,4,5-tetrachloro-1H-pyrrol-1yl) acetamide

A solution of guanidine hydrochloride (2.3, 0.024 mol) and sodium ethoxide (from 0.55 g. of sodium) in ethanol (20 cm$^3$) was stirred at room temperature for 1 h. The precipitated sodium chloride was removed by filtration and washed with ethanol (5 cm$^3$). Methyl (2,3,4,5-tetrachloro-1H-pyrrol-1-yl)acetate (4.8 g.) was added to the combined filtrate and washings obtained above and the solution stirred for 3 h., then cooled in ice and the precipitated title product collected by filtration (1.5 g.). A further 0.3 g. of product was obtained by evaporation of the mother liquors. The two crops were combined, crystallised from isopropyl alcohol and then treated with ethanolic hydrogen chloride to give 1.5 g. of pure hydrochloride of the title compound, m.p. 215°–217° C.

EXAMPLE 3

2,5-Dichloro-N-(2-hexahydropyrimidinylidene)-1H-pyrrol-1-acetamide

By a procedure analogous to Example 8, 2-amino-1,4,5,6-tetrahydropyrimidine is reacted with methyl (2,5-dichloro-1H-pyrrol-1-yl)acetate to give the title compound.

EXAMPLE 14

N-Diaminomethylene-(2,3,5-trimethyl-1H-pyrrol-1-yl)-acetamide

By a procedure analogous to Example 1, 3-methylhexan-2,5-dione (J. Amer. Chem. Soc., 1929, 51, 3514) is reacted with glycine methyl ester to give methyl(2,3,5-trimethyl-1H-pyrrol-1-yl)acetate.

By a procedure analogous to Example 2, guanidine is reacted with methyl (2,3,5-trimethyl-1H-pyrrol-1-yl) acetate to give the title compound.

EXAMPLE 15

N-Diaminomethylene-(2,5-ditrifluoromethyl-1H-pyrrol-1-yl)-acetamide

By the general procedures described in Arch. Pharm., 1959, 292, 508, for conversion of β-keto esters nitro γ-diketones, ethyl 4,4,4-trifluoroacetate is converted to 1,1,1,6,6,6-hexafluorohexan-2,5-dione.

By a procedure analogous to Example 1, 1,1,1,6,6,6-hexafluorohexan-2,5-dione is reacted with glycine methyl ester to give methyl (2,5-ditrifluoromethyl-1H-pyrrol-1-yl)acetate.

By a procedure analogous to Example 2, guanidine is reacted with methyl (2,5-ditrifluoromethyl-1H-pyrrol-2-yl)acetate to give the title compound.

EXAMPLE 16

N-Diaminomethylene-(trans-2,5-dimethylpyrrolidin-1-yl)-acetamide

By a procedure analogous to Example 6, methyl bromoacetate is reacted with trans-2,5-dimethylpyrrolidine (J. Amer. Chem. Soc. 1951, 73, 5230) to give methyl (trans-2,5-dimethylpyrrolidin-1-yl)acetate.

By a procedure analogous to Example 7, guanidine is reacted with methyl (trans-2,5-dimethyl-pyrrolidin-1-yl)acetate to yield the title compound.

I claim:

1. A compound selected from the group consisting of a guanidine of the formula

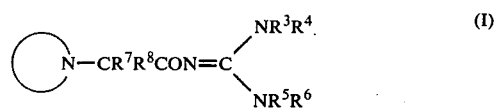

and a pharmaceutically acceptable acid addition salt thereof, where

represents

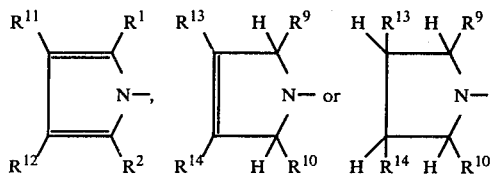

wherein $R^1$ and $R^2$ which may be the same or different each represent hydrogen, lower alkyl, trifluoromethyl or halogen and $R^{11}$ and $R^{12}$ which may be the same or different each represents hydrogen, lower alkyl, trifluoromethyl or halogen with the proviso that when one or both $R^{11}$ and $R^{12}$ groups represent halogen then $R^1$ and $R^2$ each represent lower alkyl, trifluoromethyl or halogen, $R^9$ and $R^{10}$ which may be the same or different each represents hydrogen, lower alkyl or trifluoromethyl and $R^{13}$ and $R^{14}$ which may be the same or different each represents hydrogen, lower alkyl, trifluoromethyl or halogen with the proviso that when one or both $R^{13}$ and $R^{14}$ groups represent halogen then $R^9$ and $R^{10}$ each represent lower alkyl or trifluoromethyl, and $R^7$ and $R^8$ are the same or different and each represent hydrogen or lower alkyl and $R^3$, $R^4$, $R^5$ and $R^6$ are the same or different and each represent hydrogen or lower alkyl.

2. A compound according to claim 1 of the formula (II)

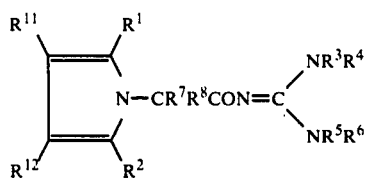

or a pharmaceutically acceptable acid addition salt thereof, wherein $R^3$, $R^4$, $R^5$, $R^6$, $R^7$ and $R^8$ have the meanings given in claim 1, $R^{11}$ and $R^{12}$ are both hydrogen and $R^1$ and $R^2$ each represent hydrogen, lower alkyl or halogen.

3. A compound according to claim 1 which is N-diaminomethylene-(2,5-dimethyl-1H-pyrrol-1-yl) acetamide or a pharmaceutically acceptable salt thereof.

4. A compound according to claim 1 which is N-diaminomethylene-1H-pyrrol-1-yl acetate or a pharmaceutically acceptable salt thereof.

5. A compound according to claim 1 which is N-diaminomethylene-(2,5-dichloro-1H-pyrrol-1-yl) acetamide or a pharmaceutically acceptable salt thereof.

6. A compound according to claim 1 which is N-diaminomethylene-(2,3,4,5-tetrachlorio-1H-pyrrol-1-yl)acetamide or a pharmaceutically acceptable acid addition salt thereof.

7. The compound according to claim 1 of the formula (III)

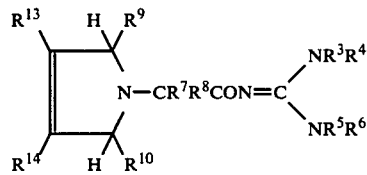

or a pharmaceutically acceptable salt thereof, wherein $R^3$, $R^4$, $R^5$, $R^6$, $R^7$ and $R^8$ have the meanings given in claim 1, $R^{13}$ and $R^{14}$ are both hydrogen and $R^9$ and $R^{10}$ are each hydrogen or lower alkyl.

8. A compound according to claim 1, which is N-diaminomethylene-(trans-2,5-dihydro-2,5-dimethyl-1H-pyrrol-1-yl)acetamide or a pharmaceutically acceptable acid addition salt thereof.

9. A compound according to claim 1 which is N-diaminomethylene-2-(trans-2,5-dimethyl-2,5-dihydro-1H-pyrrol-1-yl)propionamide or a pharmaceutically acceptable acid addition salt thereof.

10. A compound according to claim 1 of formula (IV)

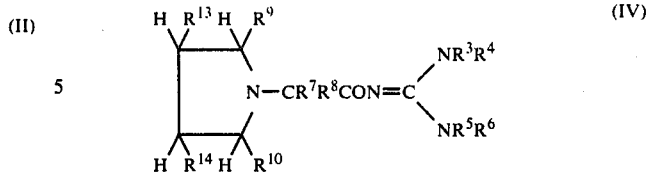

or a pharmaceutically acceptable acid addition salt thereof, wherein $R^3$, $R^4$, $R^5$, $R^6$, $R^7$ and $R^8$ have the meanings given in claim 1, $R^{13}$ and $R^{14}$ are both hydrogen and $R^9$ and $R^{10}$ are each hydrogen or lower alkyl.

11. A pharmaceutical composition having blood pressure lowering or anti-ulcer activity comprising an effective amount of a compound selected from the group consisting of a guanidine of the formula

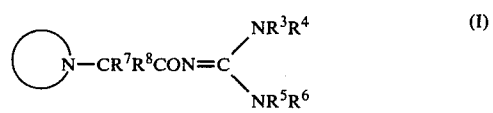

and a pharmaceutically acceptable acid addition salt thereof, where

 represents

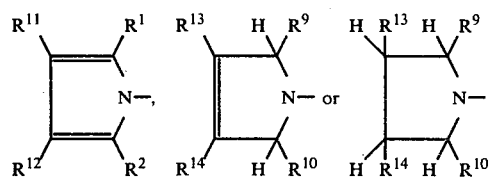

wherein $R^1$ and $R^2$ which may be the same or different each represent hydrogen, lower alkyl, trifluoromethyl or halogen and $R^{11}$ and $R^{12}$ which may be the same or different each represents hydrogen, lower alkyl, trifluoromethyl or halogen with the proviso that when one or both $R^{11}$ and $R^{12}$ groups represent halogen then $R^1$ and $R^2$ each represent lower alkyl, trifluoromethyl or halogen, $R^9$ and $R^{10}$ which may be the same or different each represents hydrogen, lower alkyl or trifluoromethyl and $R^{13}$ and $R^{14}$ which may be the same or different each represents hydrogen, lower alkyl, trifluoromethyl or halogen with the proviso that when one or both $R^{13}$ and $R^{14}$ groups represent halogen then $R^9$ and $R^{10}$ each represent lower alkyl or trifluoromethyl, and $R^7$ and $R^8$ are the same or different and each represent hydrogen or lower alkyl and $R^3$, $R^4$, $R^5$ and $R^6$ are the same or different and each represent hydrogen or lower alkyl in association with a pharmaceutically acceptable carrier.

* * * * *

UNITED STATES PATENT AND TRADEMARK OFFICE
CERTIFICATE OF CORRECTION

PATENT NO. : 4,140,793
DATED : February 20, 1979
INVENTOR(S) : Terence James Ward It is certified that error appears in the above-identified patent and that said Letters Patent are hereby corrected as shown below:

Column 1, line 29, "the trifluoro" should read -- trifluoro --,

Column 2, line 15, "$R^{12}$ the" should read -- $R^{12}$ have the --,

Column 2, line 17, "methyl ethyl" should read -- methyl, ethyl --,

Column 2, line 56, "(eg methyl)," should read -- (e.g. methyl, --,

Column 5, line 47, "acid" should read -- acid) --,

Column 15, line 20, "1 yl)" should read -- 1-yl --,

Column 15, line 36, "Example 3" should read -- Example 13 --,

Claim 4, line 2, "acetate" should read -- acetamide --,

Claim 6, line 2, "tetrachlorio" should read -- tetrachloro --,

Claim 7, line 1, "the compound" should read -- A compound --.

Signed and Sealed this

Twenty-first Day of October 1980

[SEAL]

Attest:

SIDNEY A. DIAMOND

Attesting Officer

Commissioner of Patents and Trademarks